US010213204B2

(12) United States Patent
Aranyi et al.

(10) Patent No.: US 10,213,204 B2
(45) Date of Patent: Feb. 26, 2019

(54) MICRO SURGICAL INSTRUMENT AND LOADING UNIT FOR USE THEREWITH

(71) Applicant: Covidien LP, Mansfield, MA (US)

(72) Inventors: Ernest Aranyi, Easton, CT (US); Stanislaw Kostrzewski, Newtown, CT (US); Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 580 days.

(21) Appl. No.: 14/873,500

(22) Filed: Oct. 2, 2015

(65) Prior Publication Data

US 2017/0095253 A1    Apr. 6, 2017

(51) Int. Cl.
*A61B 17/10* (2006.01)
*A61B 17/068* (2006.01)
*A61B 17/072* (2006.01)

(52) U.S. Cl.
CPC .......... *A61B 17/105* (2013.01); *A61B 17/068* (2013.01); *A61B 17/072* (2013.01)

(58) Field of Classification Search
CPC .... A61B 17/072; A61B 17/068; A61B 17/105
USPC ........................................... 227/175.1–182.1
See application file for complete search history.

(56) References Cited

U.S. PATENT DOCUMENTS

| | | |
|---|---|---|
| 3,079,606 A | 3/1963 | Bobrov et al. |
| 3,490,675 A | 1/1970 | Green et al. |
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |

(Continued)

FOREIGN PATENT DOCUMENTS

| | | |
|---|---|---|
| AU | 198654765 | 9/1986 |
| CA | 2773414 A1 | 11/2012 |

(Continued)

OTHER PUBLICATIONS

European Search Report EP 16 19 1679 dated Mar. 6, 2017.

(Continued)

*Primary Examiner* — Thanh Truong
*Assistant Examiner* — Xavier A Madison

(57) ABSTRACT

A loading unit for engagement with a surgical instrument. The loading unit includes a proximal body portion, an end effector, an actuation sled, and pushers. The actuation sled is longitudinally translatable within a cartridge assembly. The pushers are disposed within the cartridge assembly. Each pusher includes a camming surface configured for engagement with the actuation sled. The camming surface of each pusher in a first row is longitudinally aligned with the camming surface of each pusher in a second row. The first row of pushers is laterally offset from the second row of pushers.

20 Claims, 16 Drawing Sheets

(56) References Cited

U.S. PATENT DOCUMENTS

| | | |
|---|---|---|
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |

(56) References Cited

U.S. PATENT DOCUMENTS

| | | |
|---|---|---|
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A * | 8/1998 | Oberlin ............ A61B 17/07207 227/176.1 |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |

(56) References Cited

U.S. PATENT DOCUMENTS

| | | |
|---|---|---|
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |

(56) References Cited

U.S. PATENT DOCUMENTS

| | | |
|---|---|---|
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Lubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |

(56) References Cited

U.S. PATENT DOCUMENTS

| | | | |
|---|---|---|---|
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 * | 7/2012 | Hess ............. A61B 17/0644 227/181.1 |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |

(56) References Cited

U.S. PATENT DOCUMENTS

| | | |
|---|---|---|
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |

(56) References Cited

U.S. PATENT DOCUMENTS

| | | |
|---|---|---|
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,851,355 B2 | 10/2014 | Aranyi et al. |
| 9,016,546 B2 | 4/2015 | Demmy et al. |
| 9,027,817 B2 | 5/2015 | Milliman et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0067460 A1 | 3/2005 | Milliman et al. |
| 2005/0103819 A1 | 5/2005 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0083807 A1* | 4/2008 | Beardsley ........ A61B 17/07207 227/175.1 |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277949 A1 | 11/2009 | Viola et al. |
| 2009/0283568 A1 | 11/2009 | Racenet et al. |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0127043 A1* | 5/2010 | Olson ............. A61B 17/07207 227/178.1 |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2010/0305552 A1 | 12/2010 | Shelton, IV et al. |
| 2011/0006099 A1 | 1/2011 | Hall et al. |
| 2011/0006101 A1 | 1/2011 | Hall et al. |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0068148 A1 | 3/2011 | Hall et al. |
| 2011/0087276 A1 | 4/2011 | Bedi et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132964 A1 | 6/2011 | Weisenburgh, II et al. |
| 2011/0139851 A1 | 6/2011 | McCuen |
| 2011/0147433 A1 | 6/2011 | Shelton, IV et al. |
| 2011/0155781 A1 | 6/2011 | Swensgard et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |

(56) References Cited

U.S. PATENT DOCUMENTS

| | | |
|---|---|---|
| 2011/0204119 A1 | 8/2011 | McCuen |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0061446 A1 | 3/2012 | Knodel et al. |
| 2012/0061450 A1 | 3/2012 | Kostrzewski |
| 2012/0074196 A1 | 3/2012 | Shelton, IV et al. |
| 2012/0074200 A1 | 3/2012 | Schmid et al. |
| 2012/0080474 A1 | 4/2012 | Farascioni |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080498 A1 | 4/2012 | Shelton, IV et al. |
| 2012/0080499 A1 | 4/2012 | Schall et al. |
| 2012/0080502 A1 | 4/2012 | Morgan et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0223123 A1 | 9/2012 | Baxter, III et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0255986 A1 | 10/2012 | Petty et al. |
| 2012/0286021 A1 | 11/2012 | Kostrzewski |
| 2012/0286022 A1 | 11/2012 | Olson et al. |
| 2012/0292369 A1 | 11/2012 | Munro, III et al. |
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0068821 A1 | 3/2013 | Huitema et al. |
| 2013/0075443 A1 | 3/2013 | Giordano et al. |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0112732 A1 | 5/2013 | Aranyi et al. |
| 2013/0112733 A1 | 5/2013 | Aranyi et al. |
| 2013/0119109 A1 | 5/2013 | Farascioni et al. |
| 2013/0126581 A1 | 5/2013 | Yates et al. |
| 2013/0126582 A1 | 5/2013 | Shelton, IV et al. |
| 2013/0126586 A1 | 5/2013 | Zhang et al. |
| 2013/0140343 A1 | 6/2013 | Knodel |
| 2013/0144333 A1 | 6/2013 | Viola |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0175316 A1 | 7/2013 | Thompson et al. |
| 2013/0186931 A1 | 7/2013 | Beardsley |
| 2013/0193188 A1 | 8/2013 | Shelton, IV et al. |
| 2013/0277410 A1 | 10/2013 | Fernandez et al. |
| 2013/0334280 A1 | 12/2013 | Krehel et al. |
| 2013/0334281 A1 | 12/2013 | Williams |
| 2014/0001232 A1 | 1/2014 | Cappola et al. |
| 2014/0001233 A1 | 1/2014 | Cappola et al. |
| 2014/0014704 A1 | 1/2014 | Onukuri et al. |

(56) References Cited

U.S. PATENT DOCUMENTS

| | | |
|---|---|---|
| 2014/0014707 A1 | 1/2014 | Onukuri et al. |
| 2014/0021242 A1 | 1/2014 | Hodgkinson et al. |
| 2014/0025046 A1 | 1/2014 | Williams et al. |
| 2014/0027492 A1 | 1/2014 | Williams |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0103092 A1 | 4/2014 | Kostrzewski et al. |
| 2014/0110453 A1 | 4/2014 | Wingardner et al. |
| 2014/0110455 A1 | 4/2014 | Ingmanson et al. |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0158741 A1 | 6/2014 | Woodard, Jr. et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203061 A1 | 7/2014 | Hodgkinson |
| 2014/0203062 A1 | 7/2014 | Viola |
| 2014/0203063 A1 | 7/2014 | Hessler et al. |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239042 A1 | 8/2014 | Simms et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263537 A1 | 9/2014 | Leimbach et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0284372 A1 | 9/2014 | Kostrzewski |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2014/0367448 A1 | 12/2014 | Cappola |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0053749 A1 | 2/2015 | Shelton, IV et al. |
| 2015/0054753 A1 | 2/2015 | Morgan et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |

FOREIGN PATENT DOCUMENTS

| | | |
|---|---|---|
| CN | 104248458 A | 12/2014 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |

(56) References Cited

FOREIGN PATENT DOCUMENTS

| | | |
|---|---|---|
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2371296 A1 | 10/2011 |
| EP | 2583630 A2 | 4/2013 |
| EP | 2586382 A2 | 5/2013 |
| EP | 2737861 A1 | 6/2014 |
| EP | 2891460 A1 | 7/2015 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51-149985 | 12/1976 |
| JP | 2001-87272 | 4/2001 |
| SU | 659146 A1 | 4/1979 |
| SU | 728848 A1 | 4/1980 |
| SU | 980703 A1 | 12/1982 |
| SU | 990220 A1 | 1/1983 |
| WO | 08302247 | 7/1983 |
| WO | 89/10094 A1 | 11/1989 |
| WO | 9210976 A1 | 7/1992 |
| WO | 9308754 A1 | 5/1993 |
| WO | 9314706 A1 | 8/1993 |
| WO | 2004/032760 A2 | 4/2004 |
| WO | 2009071070 A2 | 6/2009 |

OTHER PUBLICATIONS

European Search Report dated Jun. 14, 2017 issued in corresponding European Patent Application No. 16191679.6.
European Examination Report dated Mar. 23, 2018 issued in corresponding EP Appln. No. 16191679.6.

* cited by examiner

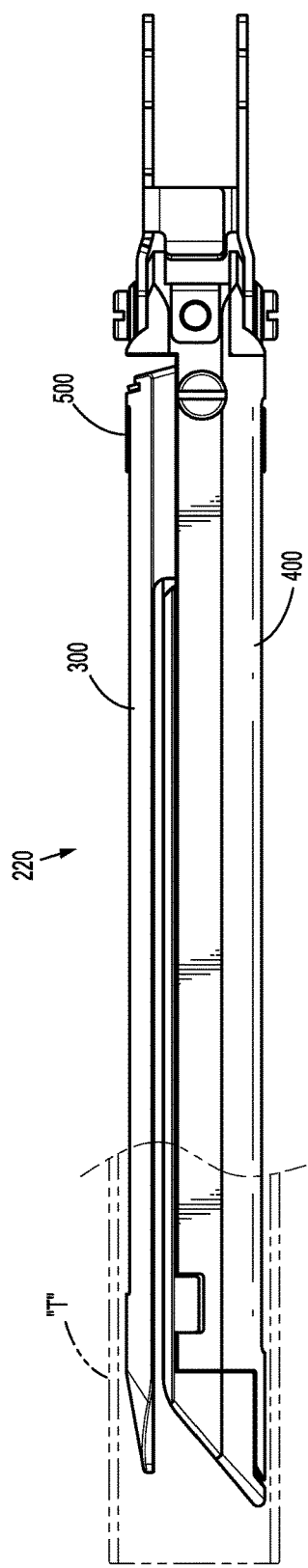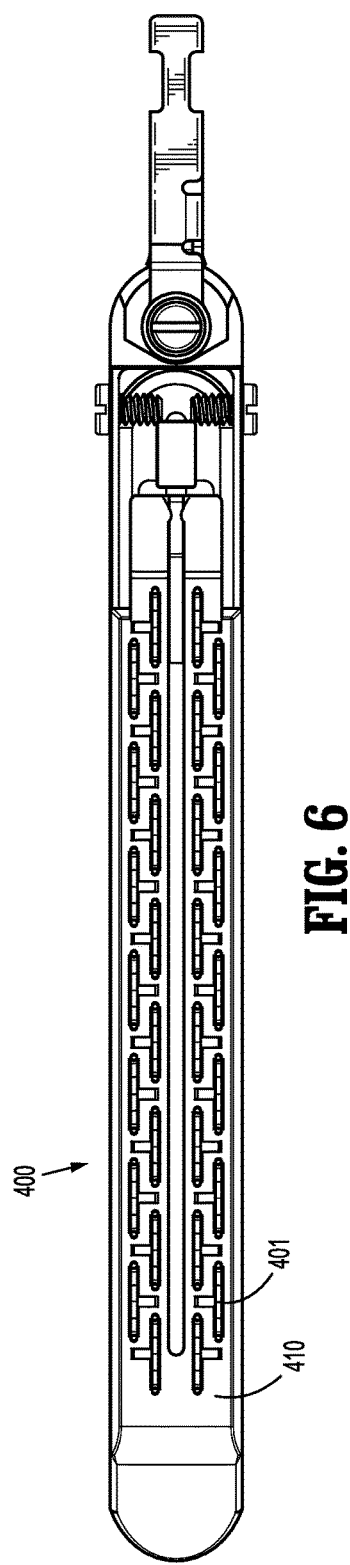
FIG. 5
FIG. 6

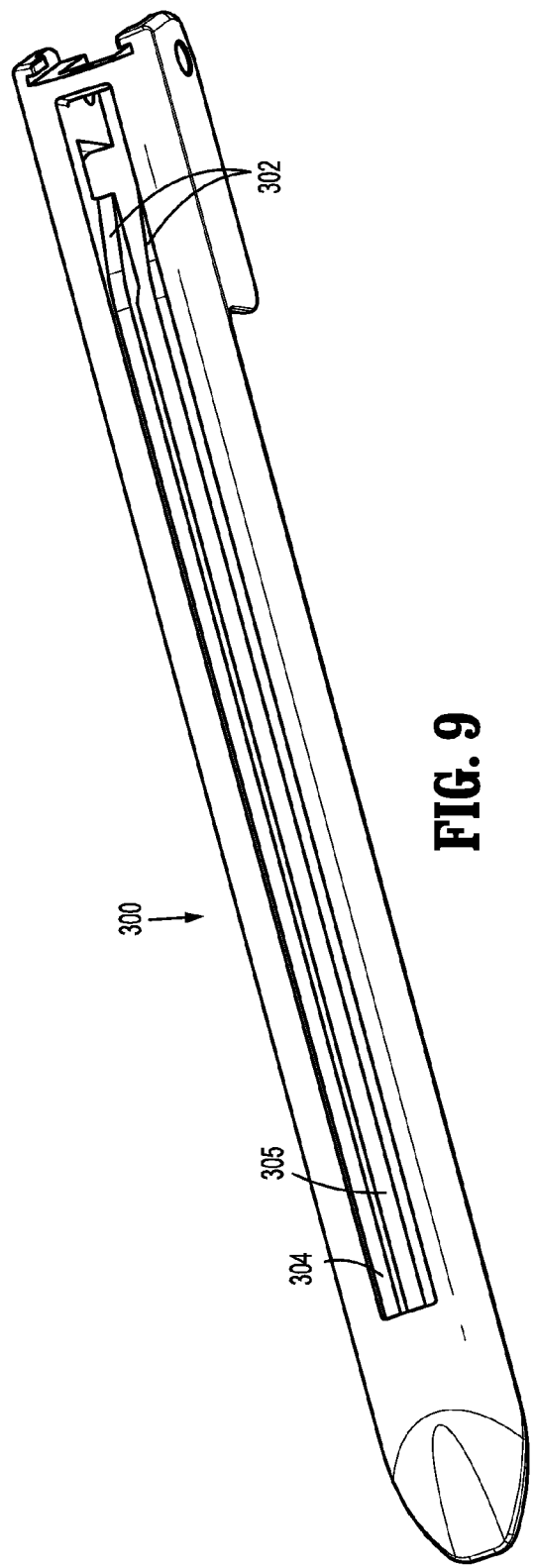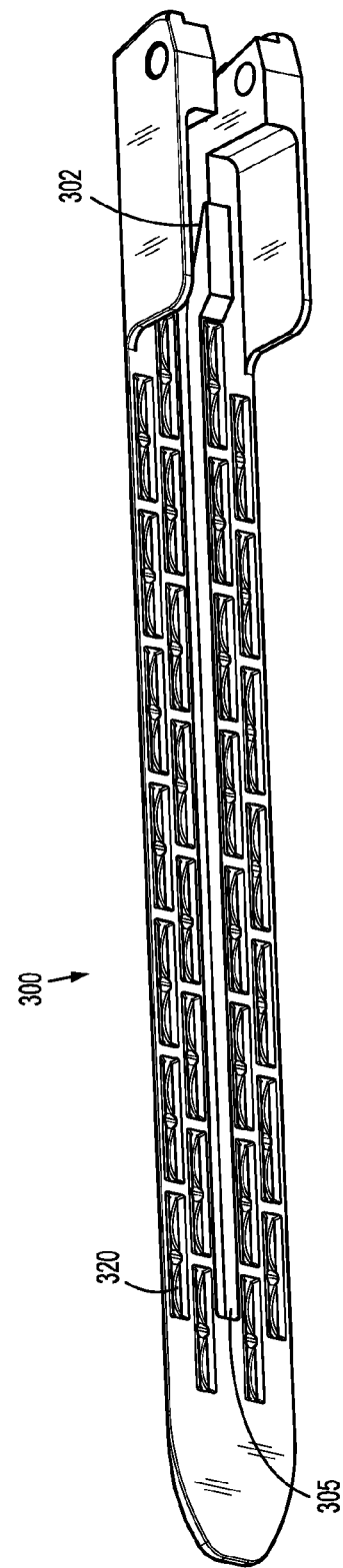

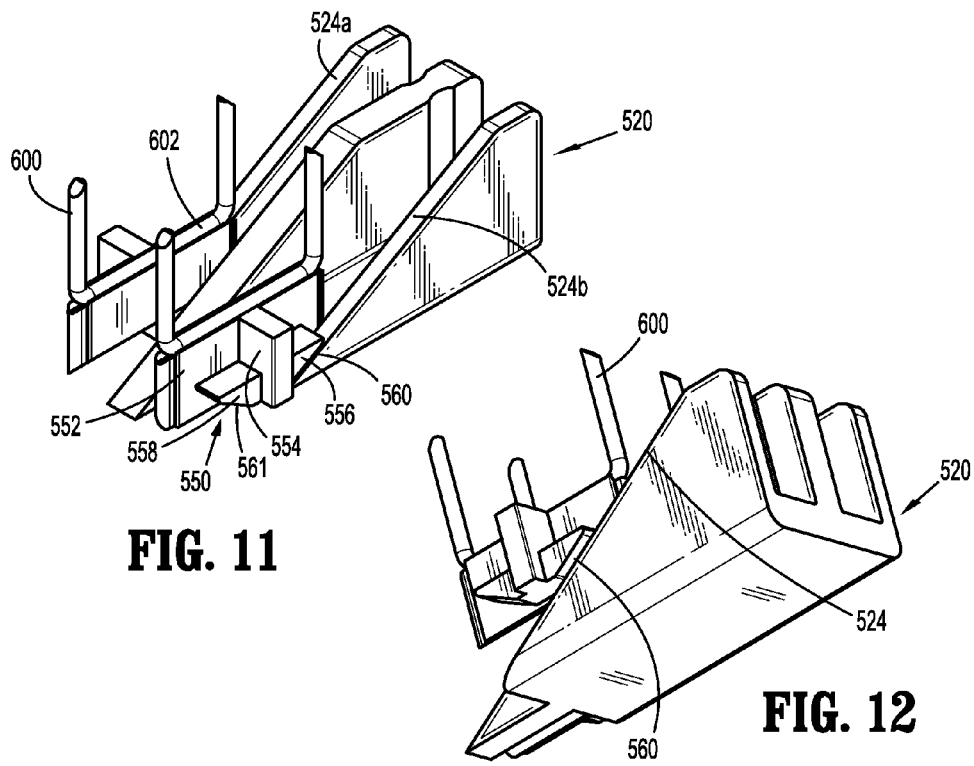
FIG. 11
FIG. 12
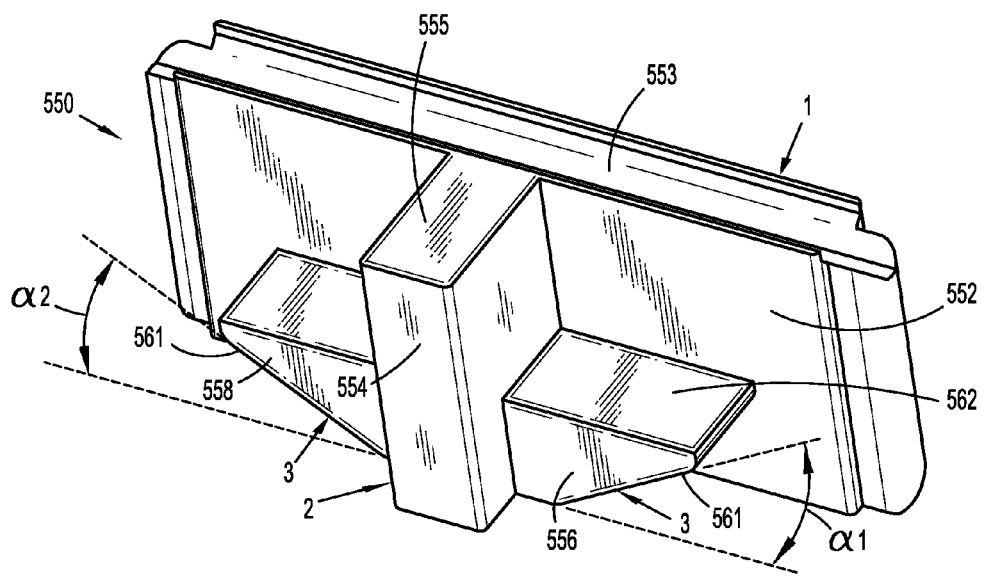
FIG. 12A

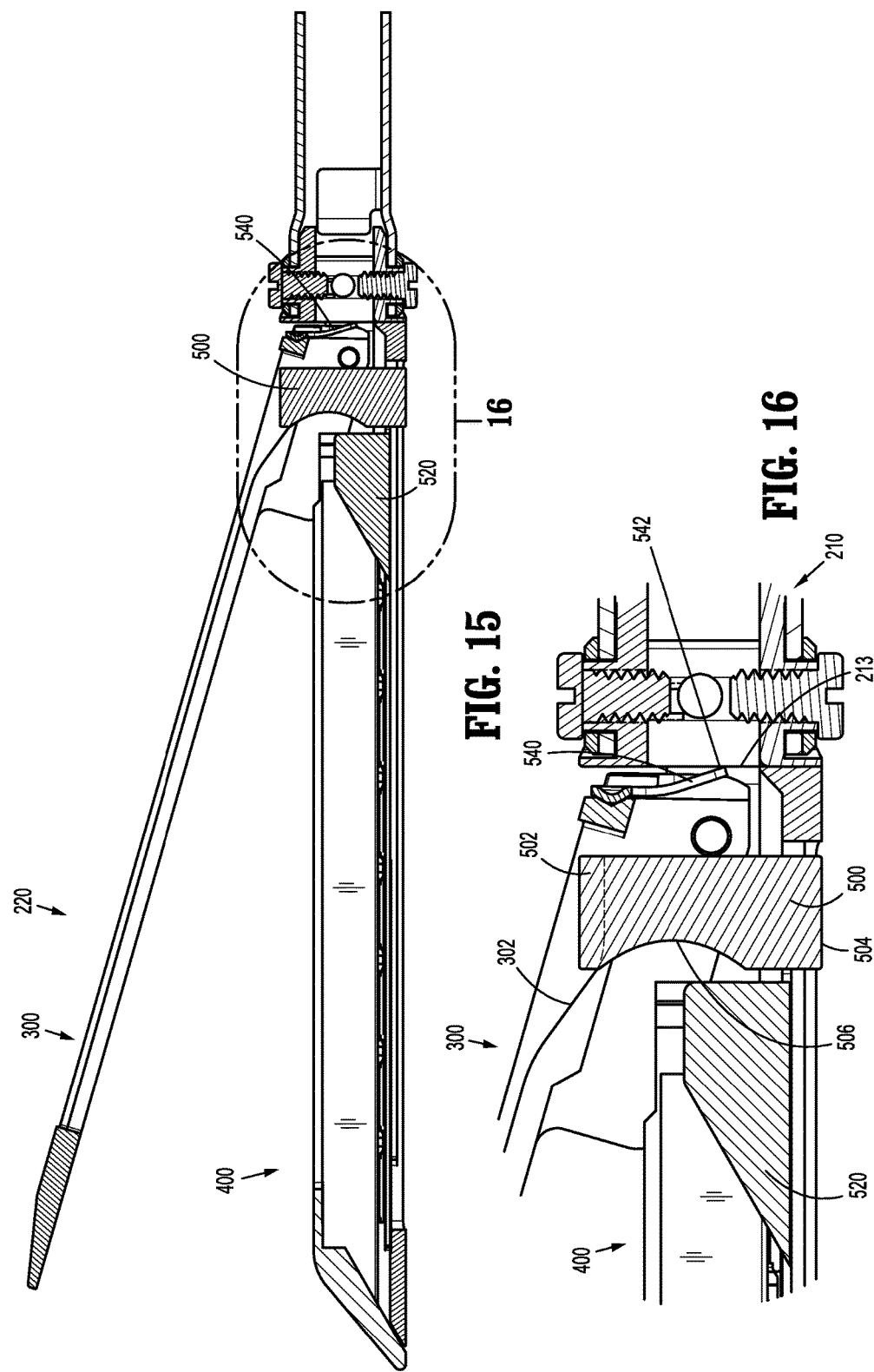

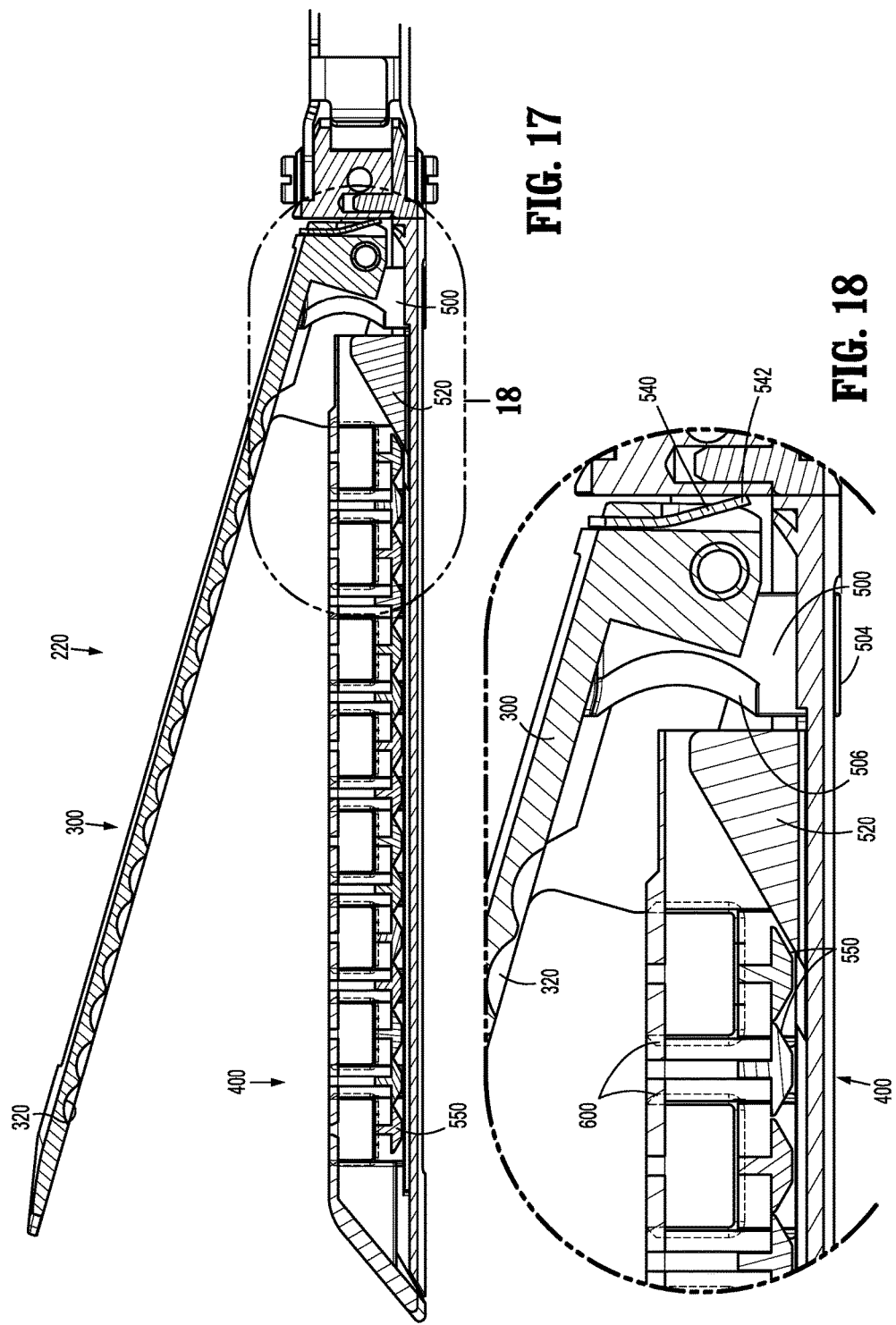

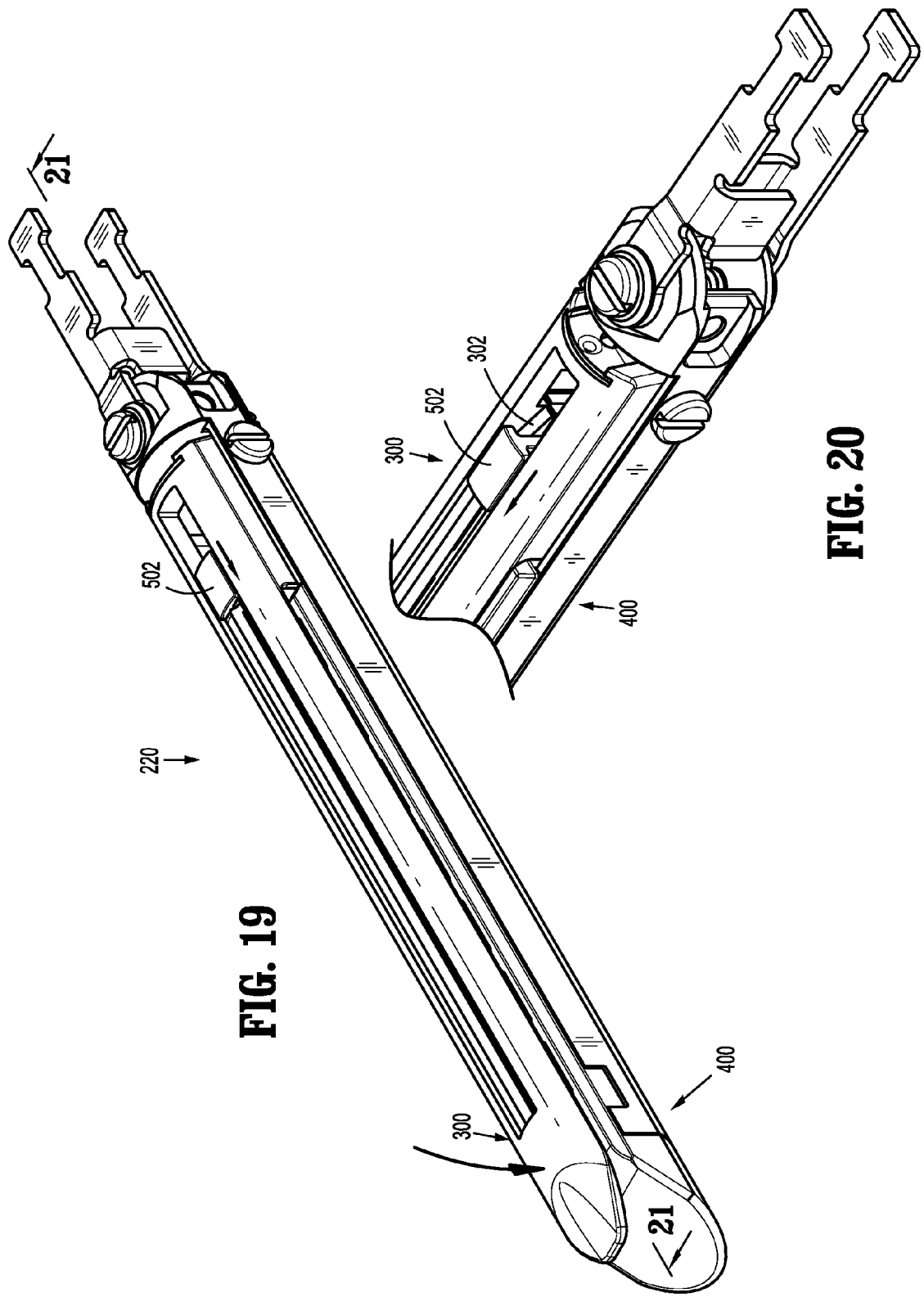

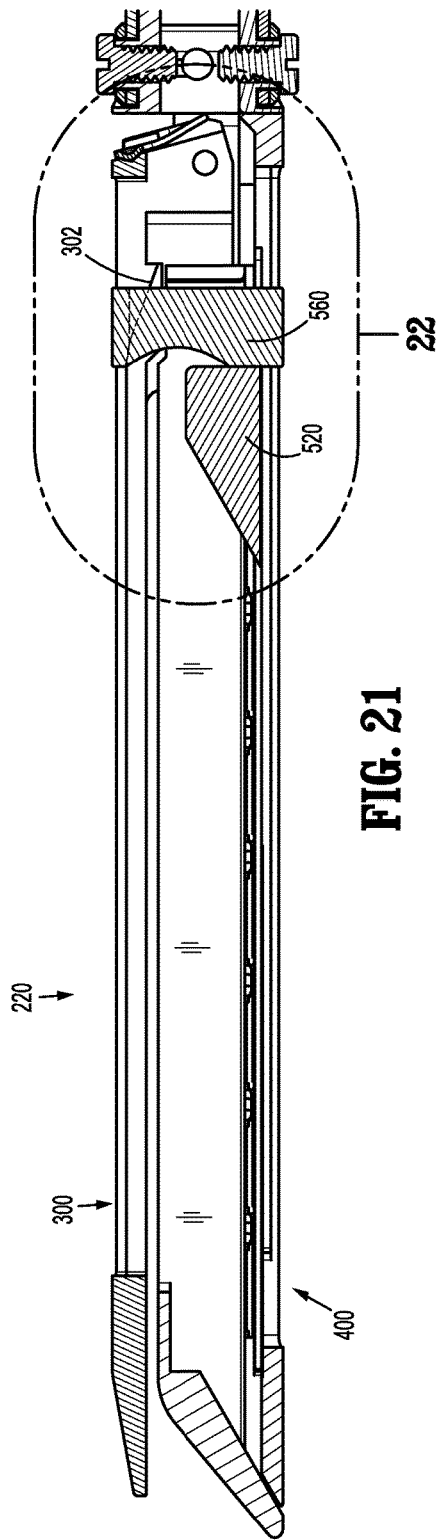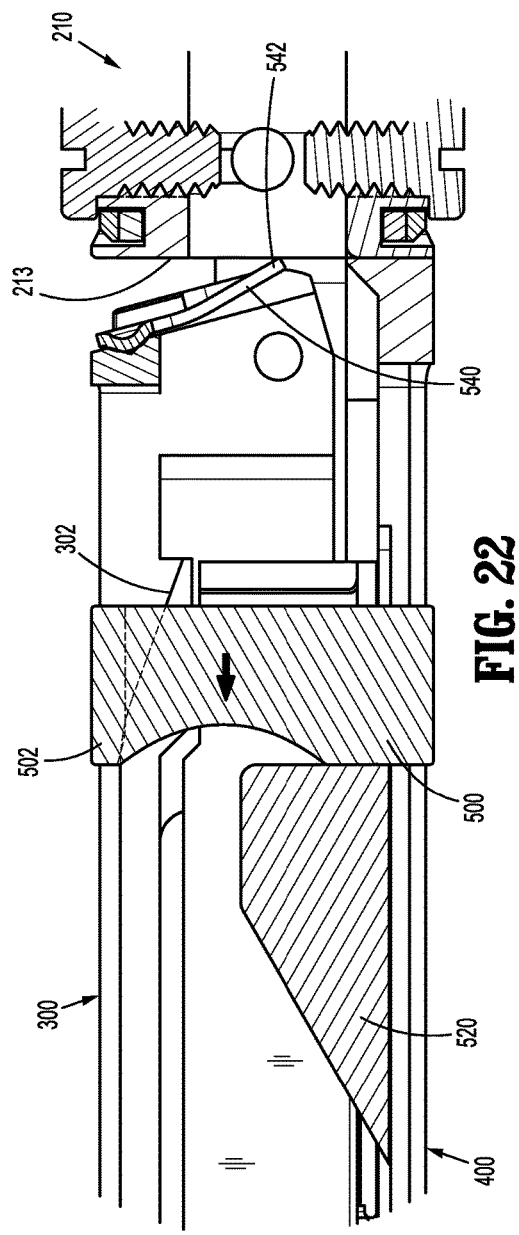

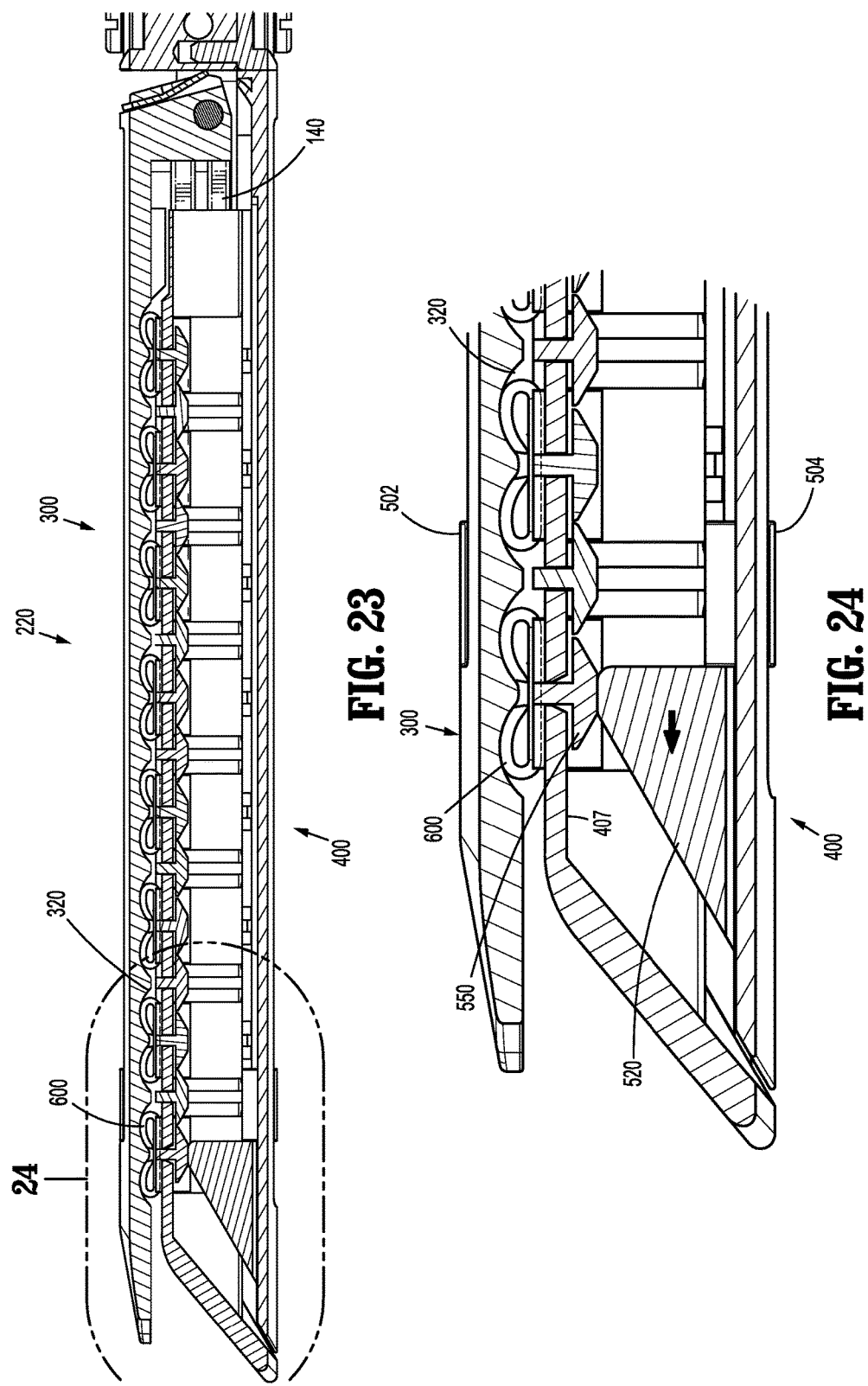

MICRO SURGICAL INSTRUMENT AND LOADING UNIT FOR USE THEREWITH

BACKGROUND

Technical Field

The present disclosure relates generally to instruments for surgically joining tissue and, more specifically, to a surgical fastening instrument and a loading unit including an end effector having a relatively small diameter.

Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical fasteners, an approximation mechanism for approximating the cartridge and anvil assemblies, and a firing mechanism for ejecting the surgical fasteners from the cartridge assembly.

Using a surgical instrument, it is common for a surgeon to approximate the anvil and cartridge members. Next, the surgeon can fire the instrument to emplace surgical fasteners in tissue. Additionally, the surgeon may use the same instrument or a separate instrument to cut the tissue adjacent or between the row(s) of surgical fasteners.

Additionally, a loading unit (e.g., a single use loading unit or a disposable loading unit) may be attached to an elongated or endoscopic portion of a surgical stapling instrument. Such loading units allow surgical stapling instruments to have greater versatility, for example. The loading units may be configured for a single use, and/or may be configured for multiple uses.

Further, end effectors and/or loading units are generally limited in size by various components contained therein. That is, while there may be a need for end effectors and/or loading units having diameters that are smaller than those typically available, the diameter of the end effector and/or loading unit is typically limited by the size, geometry and/or orientation of the staple pushers, I-beam, actuation sled, and fasteners, for example, contained therein.

SUMMARY

The present disclosure relates to a loading unit configured for engagement with a surgical instrument. The loading unit includes a proximal body portion, an end effector, an actuation sled, and pushers. The proximal body portion defines a longitudinal axis. The end effector is disposed in mechanical cooperation with the proximal body portion, and includes a cartridge assembly and an anvil assembly. One of the cartridge assembly and the anvil assembly is movable with respect to the other of the cartridge assembly and the anvil assembly between an open position and an approximated position to capture tissue therebetween. The cartridge assembly is configured to house fasteners therein. The actuation sled is longitudinally translatable within the cartridge assembly. The pushers are disposed within the cartridge assembly. The pushers are arranged in first and second rows. Each pusher includes a camming surface configured for engagement with the actuation sled. The camming surface of each pusher in the first row is longitudinally aligned with the camming surface of each pusher in the second row. The first row is laterally offset from the second row.

In disclosed embodiments, the one camming surface of each pusher includes a first camming surface and a second camming surface. It is further disclosed that the actuation sled is configured to contact the first camming surface of each pusher in the first row during distal translation of the actuation sled, and that the actuation sled is configured to contact the second camming surface of each pusher in the second row during distal translation of the actuation sled. Additionally, the second camming surface of each pusher in the first row is spaced apart from the actuation sled during distal translation of the actuation sled, and the first camming surface of each pusher in the second row is spaced apart from the actuation sled during distal translation of the actuation sled.

It is also disclosed that the pushers are arranged in a third row and a fourth row. Further, the actuation sled includes a first wedge and a second wedge. Distal translation of the actuation sled causes the first wedge to contact the camming surface of each pusher in the first row and the second camming surface of each pusher in the second row. Distal translation of the actuation sled causes the second wedge to contact the first camming surface of each pusher in the third row and the second camming surface of each pusher in the fourth row.

It is further disclosed that an outer-most diameter of the end effector is about 5 mm.

In disclosed embodiments, the loading unit includes a plurality of T-shaped retention slots extending through a tissue-contacting surface of the cartridge assembly.

It is also disclosed that each pusher in the first row is disposed in a first orientation, and each pusher in the second row is disposed in a second orientation. The first orientation is offset 180° from the second orientation.

Further, it is disclosed that each pusher in the first row is the same as each pusher in the second row.

In disclosed embodiments, the first camming surface is disposed at a first angle with respect to the longitudinal axis, the second camming surface is disposed at a second angle with respect to the longitudinal axis, and the first angle is the same as the second angle. It is disclosed that the first angle is between about 20° and about 40°.

It is further disclosed that each pusher includes a body portion including an upper edge configured to engage a fastener, a lateral extension extending perpendicularly from the body portion, a first leg extending in a first direction from the lateral extension and having a first camming surface, and a second leg extending in a second direction from the lateral extension and having a second camming surface. The upper edge of the lateral extension is co-planar with the upper edge of the body portion.

The present disclosure also relates to a pusher for use with a surgical instrument. The pusher includes a body portion, a lateral extension, a first leg and a second leg. The body portion includes an upper edge configured to engage a fastener. The lateral extension extends perpendicularly from the body portion. The first leg extends in a first direction from the lateral extension and includes a first camming surface. The second leg extends in a second direction from the lateral extension and includes a second camming surface.

In disclosed embodiments, an upper edge of the lateral extension is co-planar with the upper edge of the body portion.

It is further disclosed that the first camming surface is disposed at a first angle with respect to the longitudinal axis, the second camming surface is disposed at a second angle with respect to the longitudinal axis, and the first angle and the second angle are the same. Additionally, it is disclosed that the first angle is between about 20° and about 40°. It is also disclosed that the first direction is opposite from the second direction.

BRIEF DESCRIPTION OF FIGURES

Various embodiments of the presently disclosed surgical instruments and loading units are disclosed herein with reference to the drawings, wherein:

FIG. 5 is a side view of the end effector of FIG. 4 in an approximated position;

FIG. 6 is a top view of a cartridge assembly of the end effector of FIG. 4;

FIGS. 9 and 10 are perspective views of an anvil assembly of the end effector of FIG. 4;

FIGS. 11 and 12 are perspective views of a sled, pushers, and fasteners of the loading unit according to the present disclosure;

FIG. 12A is a perspective view of a pusher of FIGS. 11 and 12;

FIG. 15 is a side cross-sectional view of portions of the end effector taken along line 15-15 of FIG. 4;

FIG. 16 illustrates the area of detail indicated in FIG. 15;

FIG. 17 is a side cross-sectional view of portions of the end effector taken along line 17-17 of FIG. 4;

FIG. 18 illustrates the area of detail indicated in FIG. 17;

FIG. 19 is a perspective view of the end effector of the present disclosure in an approximated position;

FIG. 20 is a perspective view of a portion of the end effector of FIG. 19;

FIG. 21 is a side cross-sectional view of the end effector of the present disclosure taken along line 21-21 in FIG. 20;

FIG. 22 illustrates the area of detail indicated in FIG. 21;

FIG. 23 is side a cross-sectional view of portions of the end effector of the present disclosure;

FIG. 24 illustrates the area of detail indicated in FIG. 23;

DETAILED DESCRIPTION

Figure 1:
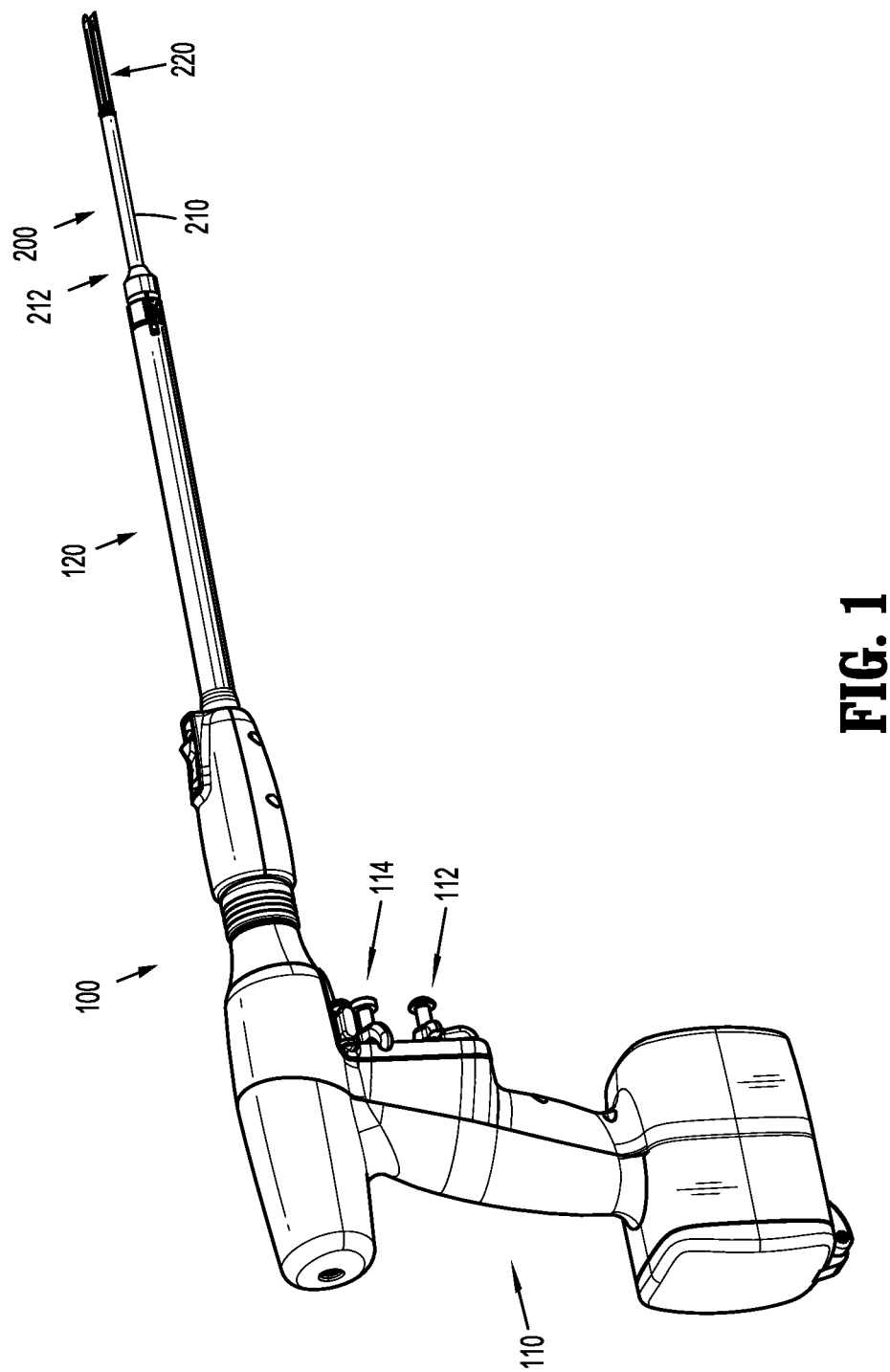
FIG. 1 is a perspective view of a surgical instrument in accordance with an embodiment of the present disclosure.

Embodiments of the presently disclosed surgical instrument, loading unit for use therewith, and cartridge assembly for use therewith, are described in detail with reference to the drawings, wherein like reference numerals designate corresponding elements in each of the several views. As is common in the art, the term "proximal" refers to that part or component closer to the user or operator, e.g., surgeon or physician, while the term "distal" refers to that part or component farther away from the user.

A surgical instrument of the present disclosure is indicated as reference numeral 100 in FIG. 1. Generally, surgical instrument 100 includes a handle assembly 110, an elongated portion 120 extending distally from handle assembly 110, and a loading unit 200 disposed adjacent a distal end of elongated portion 120. While FIG. 1 illustrates surgical instrument 100 including a powered handle assembly, other types of handles can be used such as, for example, motor-driven, hydraulic, pivoting, ratcheting, etc. As used herein, "handle assembly" encompasses all types of handle assemblies. Loading unit 200 is releasably attachable to elongated portion 120 of surgical stapling instrument 100, e.g., to allow surgical instrument 100 to have greater versatility. This arrangement allows the clinician to select a particular loading unit 200 for a given procedure. As used herein, "loading unit" encompasses both single use loading units ("SULU") and disposable loading units ("DLU"). Additionally or alternatively, surgical instrument 100 may have a cartridge that is removable and replaceable in the reusable jaws of the instrument.

Examples of loading units for use with a surgical stapling instrument are disclosed in commonly-owned U.S. Pat. No. 5,752,644 to Bolanos et al., the entire contents of which are hereby incorporated by reference herein. Further details of an endoscopic surgical stapling instrument are described in detail in commonly-owned U.S. Pat. No. 6,953,139 to Milliman et al., the entire contents of which are hereby incorporated by reference herein.

Figure 7:
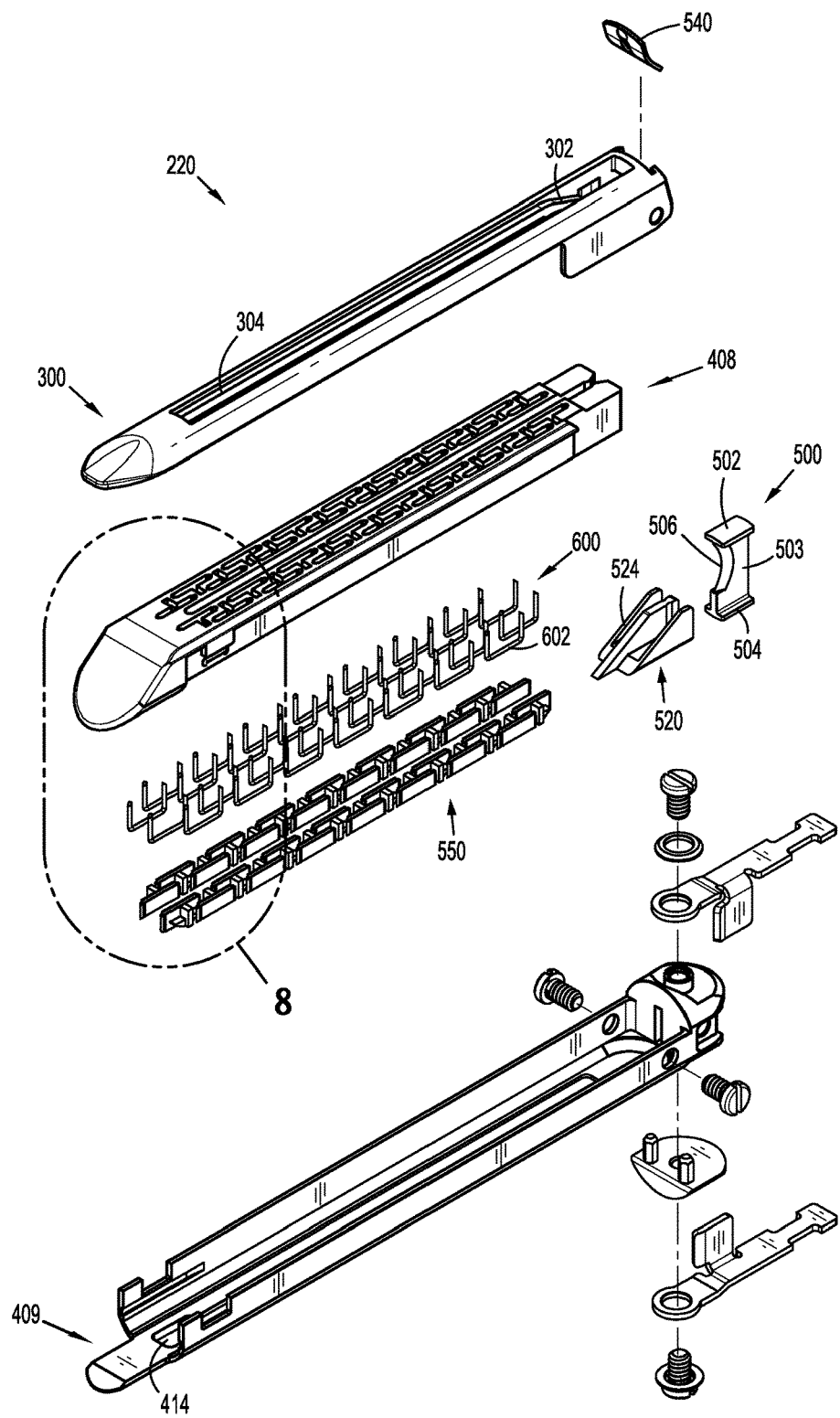
FIG. 7 is an assembly view of the end effector of FIG. 4.

In surgical instrument 100 in accordance with the present disclosure, a firing rod (not explicitly shown) is moved distally through actuation of handle assembly 110 to deploy fasteners 600 (FIG. 7). With reference to the embodiment illustrated in FIG. 1, at least a partial actuation of first switch 112 or second switch 114 translates the firing rod longitudinally. Distal translation of the firing rod causes distal translation of a knife bar 140 (FIG. 23), which causes distal translation of a clamping member 500 to approximate at least one jaw member with respect to the other, as discussed in further detail below. Further, distal translation of clamping member 500 (FIG. 2) causes corresponding translation of an actuation sled 520 (FIG. 16), which results in pushers 550 causing the ejection of fasteners 600 (FIG. 17) from pockets 401 (FIG. 6) of a cartridge assembly 400.

Figure 2:
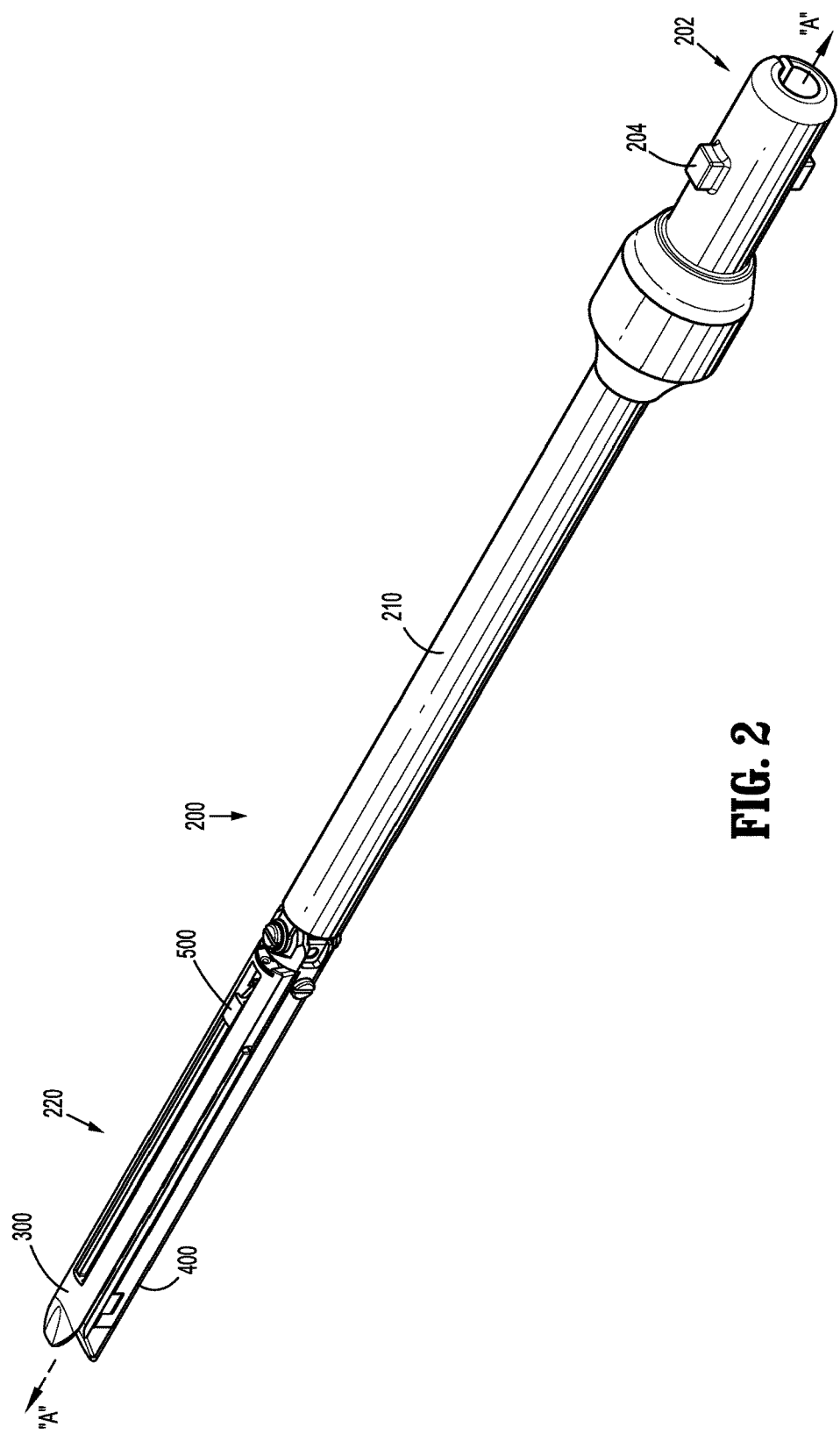
FIG. 2 is a perspective view of a loading unit having an end effector in accordance with the present disclosure.
Figure 3:
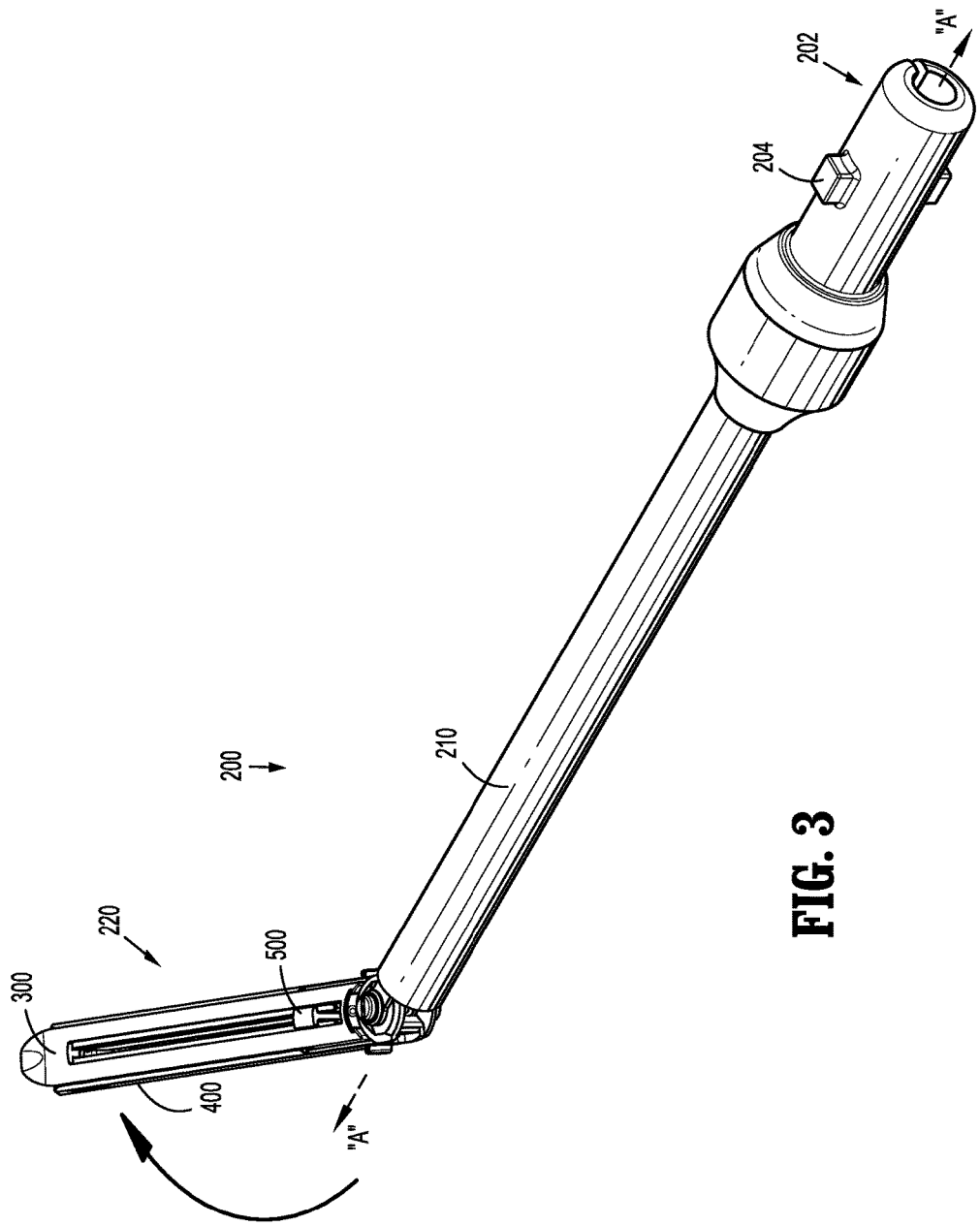
FIG. 3 is a perspective view of the loading unit of FIG. 2 illustrating the end effector disposed in an articulated position.

With additional reference to FIGS. 2 and 3, loading unit 200 of the present disclosure is shown. Loading unit 200 includes a proximal body portion 210 defining a longitudinal axis "A-A," and a tool assembly or end effector 220 including a first jaw member or anvil assembly 300 and a second jaw member or cartridge assembly 400. Cartridge assembly 400 includes a cartridge 408 disposed within a cartridge channel 409 (FIG. 7). Proximal body portion 210 is configured to be removably attached to elongated portion 120 of surgical instrument 100 as will be discussed in detail hereinbelow. As shown in FIG. 3, end effector 220 is pivotable with respect to the longitudinal axis "A-A."

Figures 25, 26:
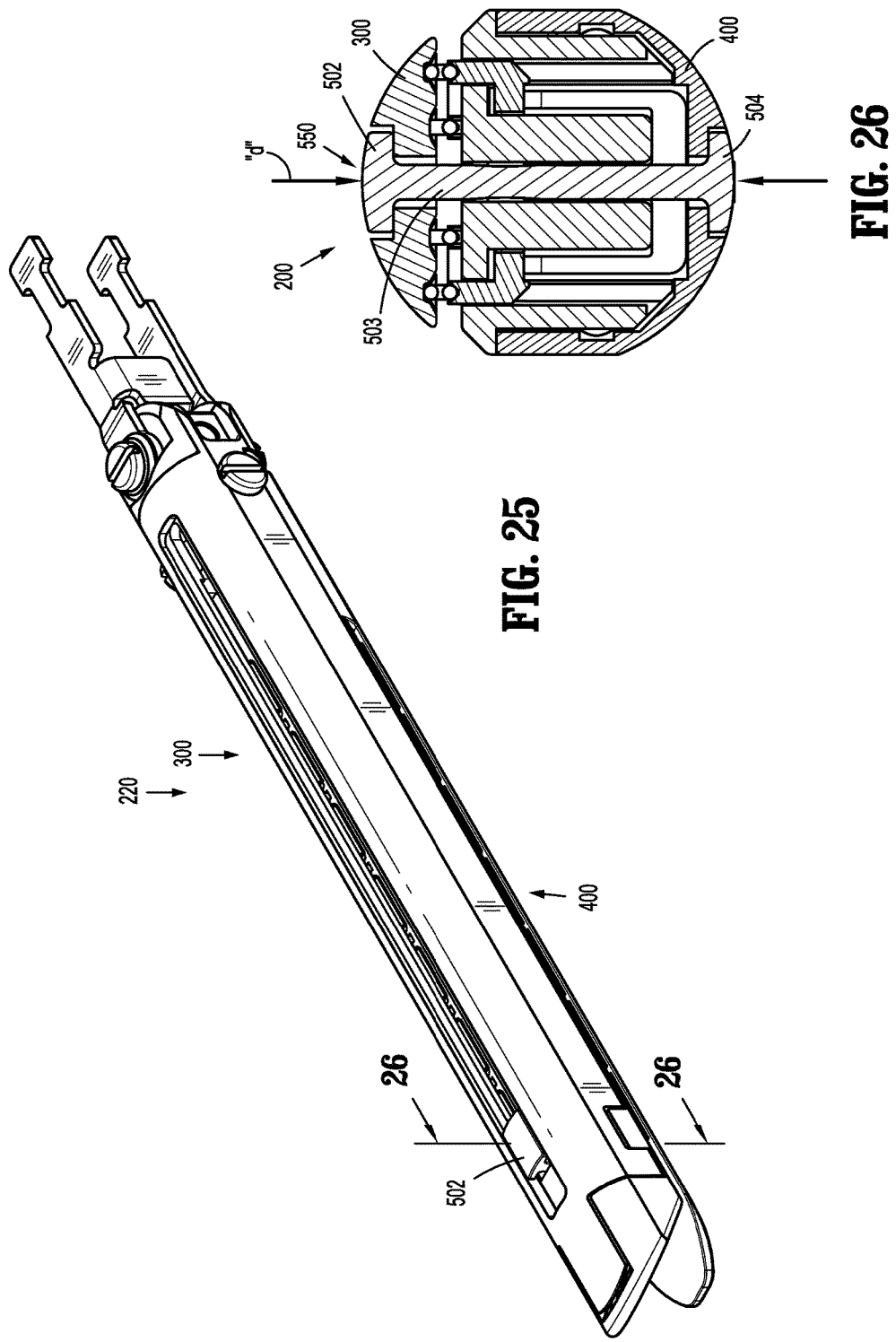
FIG. 25 is a perspective view of the end effector of the present disclosure in an approximated position.
FIG. 26 is an end cross-sectional view of the end effector of the present disclosure taken along line 26-26 in FIG. 25.

Referring now to FIG. 26, various features of loading unit 200 disclosed herein allow loading unit 200 to have a relatively small diameter "d" (such as, for example, about 4 mm, about 5 mm, about 6 mm, about 7 mm or about 8 mm) as compared with more conventional instruments having diameters of about 12 mm. The diameter "d" of the loading unit 200, and end effector 220 in particular, is measured between a radially outer-most wall of anvil assembly 300 (or top portion 502 of clamping member) and a radially outermost wall of cartridge assembly 400 (or bottom portion 504 of clamping member 500). Such a low profile allows loading unit 200 to be inserted into trocars "T" (shown in phantom in FIG. 5) or other access devices having similar inner diameters. It is contemplated that the presently disclosed end effector 220 can be inserted into openings in body tissue (e.g., incision or naturally occurring orifice) having a comparable diameter. As can be appreciated, such low profile loading units 200 are useful in pediatric surgeries and/or other thin tissue locations, for example. Additionally, in the illustrated embodiments, a proximal portion 212 of proximal body portion 210 of loading unit 200 is sized and configured to engage elongated portion 120 of surgical instrument 100 (FIG. 1) having a larger-diameter elongated portion 120 (e.g., between about 7 mm and about 12 mm), thus enabling greater versatility by allowing the loading unit 200 to be coupled to instruments having an elongated portion 120 with an outer diameter between about 7 mm and about 12 mm.

More particularly, with reference to FIG. 2, an insertion tip 202 of loading unit 200 is linearly inserted into the distal end of elongated portion 120 of surgical stapling instrument 100 (FIG. 1). Nubs 204 of insertion tip 202 move linearly through slots formed adjacent the distal end of elongated portion 120. Subsequently, loading unit 200 is rotated about the longitudinal axis "A-A" such that nubs 204 move transversely with respect to longitudinal axis "A-A" through the slots within elongated portion 120. Additionally, during engagement of loading unit 200 and elongated portion 120, the firing rod of handle portion 110 engages knife bar 140 (FIG. 23) of loading unit 200.

Figure 4:
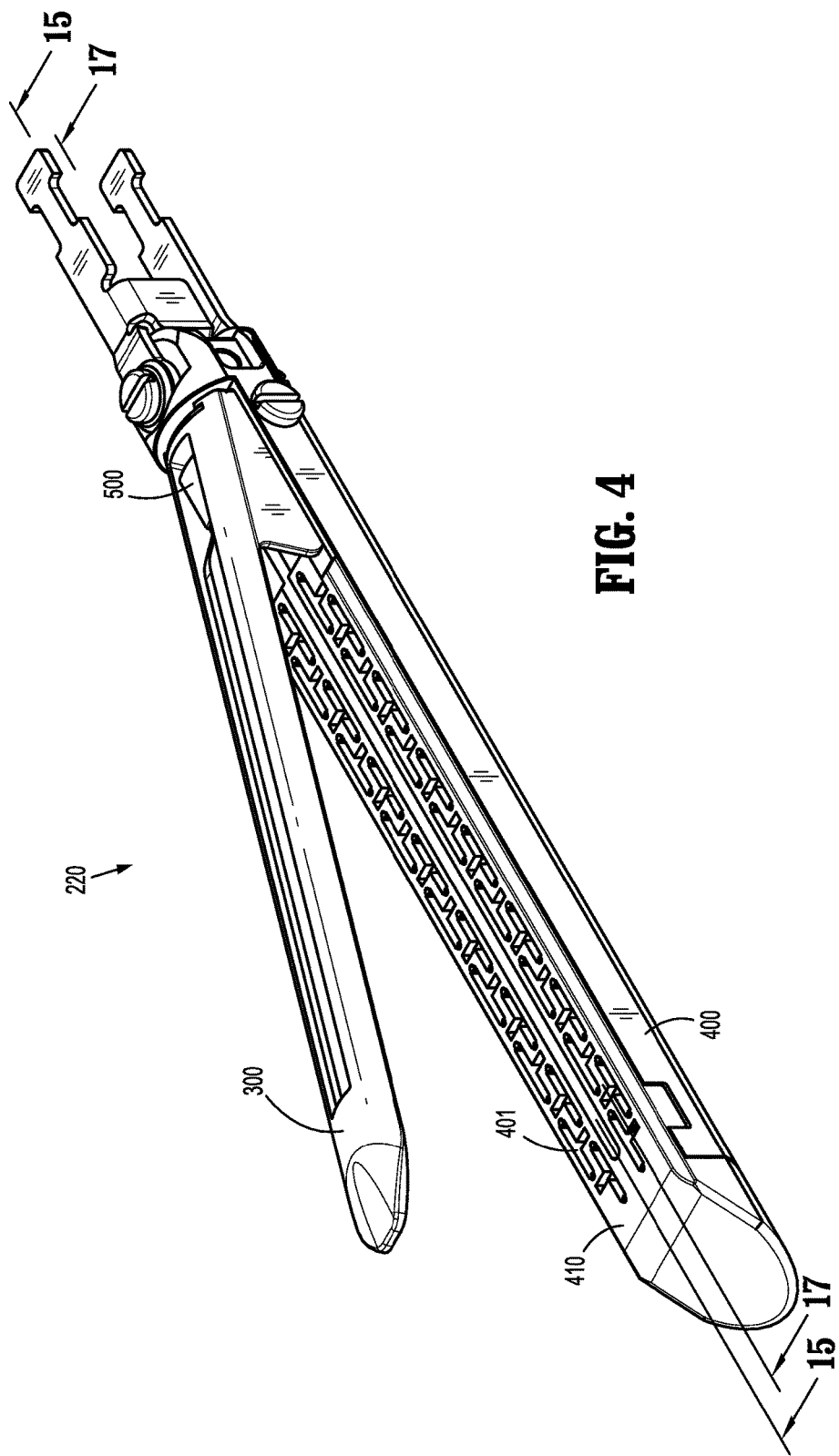
FIG. 4 is a perspective view of the end effector of FIG. 3 in an open position.

With reference to FIGS. 7 and 26, clamping member 500 includes an I-shaped cross-section, including a top portion 502, which is configured to engage anvil assembly 300, a bottom portion 504, which is configured to engage cartridge assembly 400, and a vertical portion 503, which connects top portion 502 and bottom portion 504 and which may include a cutting edge 506 on its distal or leading surface. Further, distal advancement of clamping member 500 through end effector 220 causes top portion 502 to contact a camming surface 302 of anvil assembly 300 (FIG. 16). Continued distal advancement of clamping member 500 thus causes anvil assembly 300 to pivot with respect to cartridge assembly 400 from its open position (FIG. 4) toward its approximated position (FIG. 5). Further, top portion 502 of clamping member 500 is advanced distally within a slot 304 within anvil assembly 300, and bottom portion 504 of clamping member 500 is distally advanced within a slot 414 within cartridge channel 409 of cartridge assembly 400 to help stabilize the jaw members with respect to each other and to help maintain a constant gap between the first and second jaw members 300, 400. Thus, a predetermined amount of distal travel of the firing rod causes approximation and stabilization of jaw members. Additionally, cutting edge 506 of clamping member 500, if included on clamping member 500, travels through a channel 305 (FIG. 9) of anvil assembly 300, a channel 405 (FIG. 8) of cartridge assembly 400, and severs tissue disposed between the jaw members (and after the tissue has been fastened, as discussed above).

Figure 13:
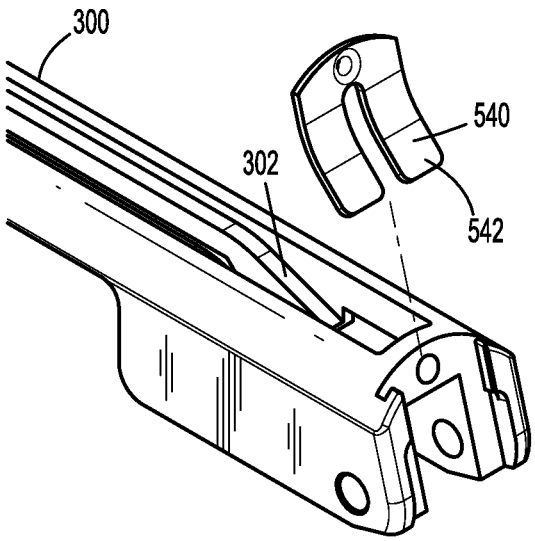
FIG. 13 is an assembly view of a portion of the anvil assembly and a spring of the loading unit of the present disclosure.
Figure 14:
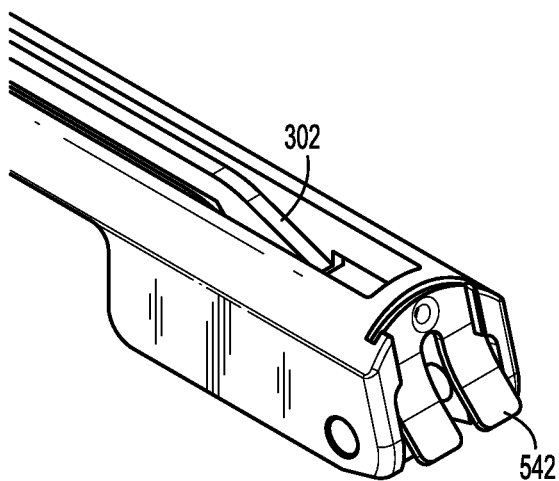
FIG. 14 is a perspective view of the proximal portion of the anvil assembly engaged with the spring of FIG. 13.

Additionally, with particular reference to FIGS. 13 and 14, a biasing element 540 is configured to bias anvil assembly 300 toward the open position. In particular, biasing element 540 (e.g., a spring) is disposed at or secured to a proximal end of anvil assembly 300. As shown in FIGS. 16 and 22, for example, biasing element 540 contacts a distal end 213 of proximal body portion 210. An end 542 (e.g., a cantilevered end) of biasing element 540 is urged proximally, thus biasing anvil assembly 300 toward its open position (FIG. 15).

With further regard to actuation sled 520, distal translation of actuation sled 520 sequentially engages a plurality of pushers 550, and causes pushers 550 to move toward tissue-contacting surface 410 (FIG. 8) of cartridge assembly 400 and eject fasteners 600 towards anvil assembly 300. Subsequent to the ejection of fasteners 600, cutting edge 506 of clamping member 500 severs the stapled tissue (FIG. 18).

With particular reference to FIGS. 11 and 12, further details of actuation sled 520 are disclosed. Actuation sled 520 includes two angled wedges 524a, 524b configured to contact either a first camming surface 560 or a second camming surface 561 of pusher 550, thus causing upper edges 553 of pushers 550 to engage fasteners 600, and subsequently cause ejection of fasteners 600 through retention cavities 450 of cartridge assembly 400 (FIG. 8), and toward respective pockets 320 (FIG. 10) of anvil assembly 300 (e.g., through tissue held between the jaw members).

Referring now to FIG. 12A, further details of pusher 550 are disclosed. Each pusher 550 includes a body portion 552, a lateral extension 554, a first leg 556, a second leg 558, a first camming surface 560, and a second camming surface 561. Each pusher 550 is positioned within cartridge assembly 400 such that body portion 552 is parallel to the longitudinal axis "A-A" (see FIGS. 2, 7 and 8). Upper edge 553 of body portion 552 is configured and dimensioned to engage a backspan 602 of fastener 600. Lateral extension 554 extends perpendicularly from body portion 552. In the illustrated embodiment an upper edge 555 of lateral extension 554 is co-planar with upper edge 553 of body portion 552.

Figure 8:
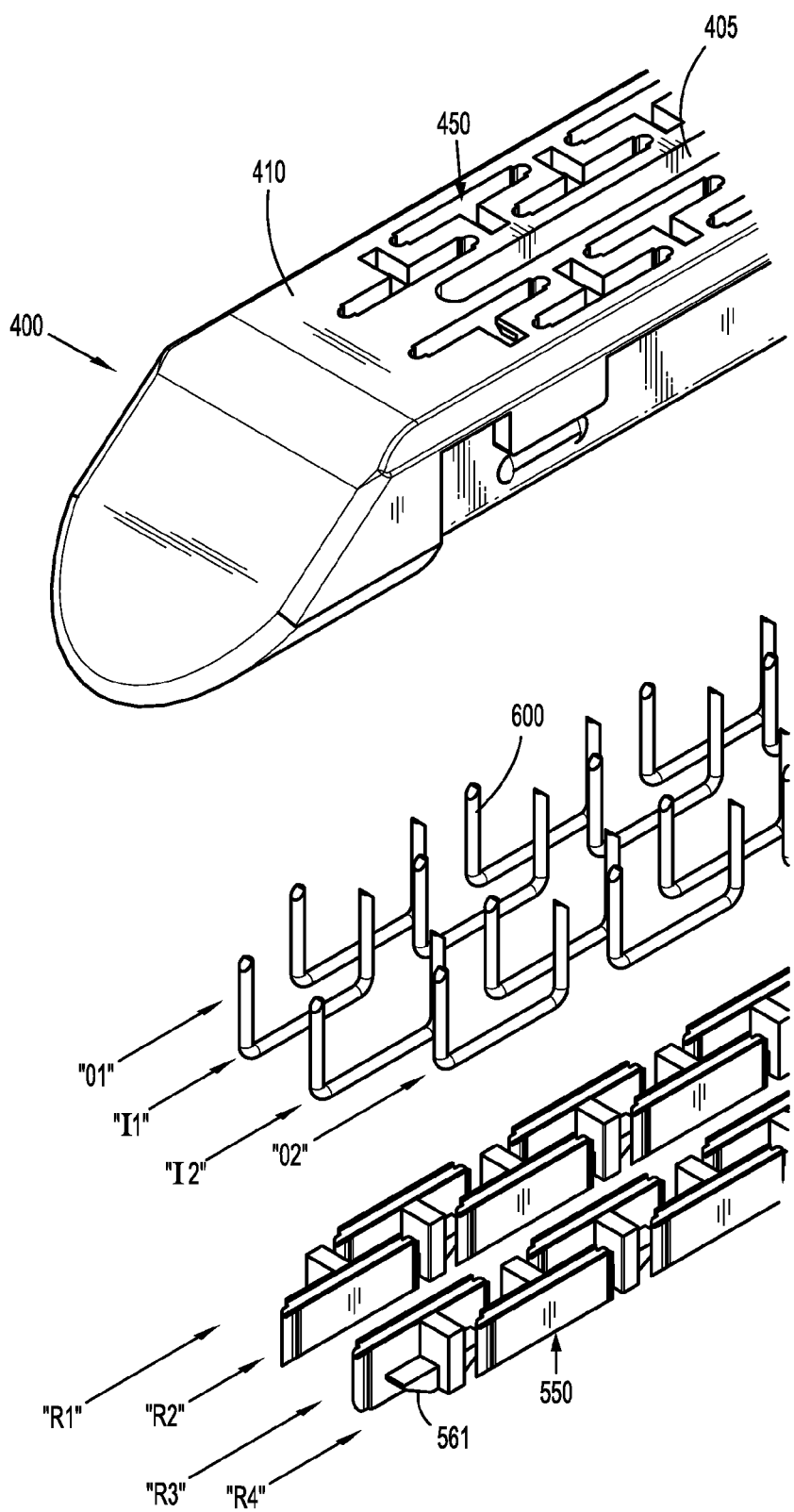
FIG. 8 illustrates the area of detail indicated in FIG. 7.

In the orientation illustrated in FIG. 12A, first leg 556 extends proximally from lateral extension 554, and second leg 558 extends distally from lateral extension 554. In this first orientation, pusher 550 is used in connection with inside rows "I1" and "I2" of fasteners 600 (FIG. 8). As can be appreciated, when the orientation of pusher 550 is rotated 180°, pusher 550 is in its second orientation and is used in connection with outside rows "O1" and "O2" of fasteners 600 (FIG. 8). Additionally, in the second orientation, first leg 556 extends distally from lateral extension 554, and second leg 558 extends proximally from lateral extension 554.

With continued reference to FIG. 12A, each of the first leg 556 and second leg 558 is generally wedge-shaped, and includes respective camming surfaces 560, 561 at its lower end and a planar surface 562 at its upper end. First camming surface 560 is disposed at a first angle α1 with respect to an axis defined by a lower surface 556a of first leg 556, and second camming surface 561 is disposed at a second angle α2 with respect to the axis defined by the lower surface 556a of first leg 556. The first angle α1 is the same as the second angle α2, and may be between about 20° and about 40°, for example. Larger and smaller angles are also contemplated.

When pusher 550 is in the first orientation (FIG. 12A), camming surface 560 of first leg 556 is configured to engage wedge 524 (wedge 524a or 524b, depending on the row, as discussed below) of actuation sled 520, while camming surface 561 of second leg 558 is configured to be free from engagement with camming surface 524 of actuation sled 520. That is, in the first orientation, camming surface 561 does not contact or engage wedge 524. When pusher 550 is in the second orientation, camming surface 561 of second leg 558 is configured to engage wedge 524 (wedge 524a or 524b, depending on the row) of actuation sled 520, while camming surface 560 of first leg 556 is configured to be free from engagement with wedge 524 of actuation sled 520. That is, in the second orientation, camming surface 560 does not contact or engage wedge 524.

Additionally, as shown in FIG. 8, pushers 550 are arranged in four longitudinal rows "R1," "R2," "R3," and "R4" where rows "R1" and "R2" are staggered on a first lateral side of channel 405, and rows "R3" and "R4" are staggered on a second lateral side of channel 405. Here, camming surface 560 of first leg 556 of pushers 550 arranged in row "R1" are longitudinally aligned with camming surface 561 of second leg 558 of pushers 550 arranged in row "R2." Similarly, camming surface 560 of first leg 556 of pushers 550 arranged in row "R3" are longitudinally aligned with camming surface 561 of second leg 558 of pushers arranged in row "R4." Accordingly, each wedge 524a, 524b of actuation sled 520 is configured to engage two rows of pushers 550. More particularly, first wedge 524a is configured to engage pushers 550 in rows "R1" and "R2," while second wedge 524b is configured to engage pushers 550 in rows "R3" and "R4."

The pushers are the same in the rows R1, R2, R3, and R4, but are arranged in opposite orientations from adjacent rows. The first leg and second leg have camming surfaces that face in opposite directions to allow the pushers to be used in R1 and R2, for example, but in opposite orientation. The lateral extensions in adjacent rows extend in opposite directions. With the pushers in adjacent rows, such as pushers in R1 and R2 for example, the lateral extensions are accommodated with a small area because the pushers (and staples) are staggered with respect to one another.

With particular reference to FIG. 12A, planar surfaces 562 of first leg 556 and second leg 558 of pusher 550 are parallel to upper edge 553 of body portion 552, but are not co-planar with upper edge 553. It is envisioned that planar surfaces 562 contact or substantially contact an undersurface 407 within cartridge assembly 400 after pushers 550 are moved or cammed by actuation sled 520 (see FIG. 24). That is, undersurface 407 within cartridge assembly 400 limits the travel of pusher 550 toward anvil assembly 300, which may be helpful for ensuring the complete and proper formation of fasteners 600, and may also be helpful to ensure pushers 550 remain within cartridge assembly 400 (e.g., before, during, and after ejection of fasteners 600).

Referring back to FIG. 8, retention cavities 450 of cartridge assembly 400 are shown. Each retention cavity 450 is T-shaped as it intersects tissue-contacting surface 410 to accommodate the travel of pusher 550 at least partially therethrough. Additionally, similar to pushers 550, adjacent rows of retention cavities 450 are longitudinally staggered from each other, and the orientation of retention cavities 450 is rotated 180° from retention cavities 450 in one adjacent row (see FIG. 8, for example). It is envisioned that the T-shape of retention cavities 450 helps maintain the lateral and longitudinal position of pushers 550 within cartridge assembly 400.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto.

What is claimed is:

1. A loading unit configured for engagement with a surgical instrument, the loading unit comprising:
   a proximal body portion;
   an end effector disposed in mechanical cooperation with the proximal body portion, the end effector including a cartridge assembly and an anvil assembly, one of the cartridge assembly and the anvil assembly being movable with respect to the other of the cartridge assembly and the anvil assembly between an open position and an approximated position to capture tissue therebetween, the cartridge assembly configured to house fasteners therein;
   an actuation sled longitudinally translatable within the cartridge assembly; and
   pushers disposed within the cartridge assembly, the pushers arranged in first and second rows, each pusher including a camming surface configured for engagement with the actuation sled, wherein the camming surface of each pusher in the first row lies within a common longitudinal axis as the camming surface of each pusher in the second row, the first row of pushers laterally offset from the second row of pushers.

2. The loading unit according to claim 1, wherein the camming surface of each pusher includes a first camming surface and a second camming surface.

3. The loading unit according to claim 2, wherein the actuation sled is configured to contact the first camming surface of each pusher in the first row during distal translation of the actuation sled, and the actuation sled is configured to contact the second camming surface of each pusher in the second row during distal translation of the actuation sled.

4. The loading unit according to claim 3, wherein the second camming surface of each pusher in the first row is spaced apart from the actuation sled during distal translation of the actuation sled, and the first camming surface of each pusher in the second row is spaced apart from the actuation sled during distal translation of the actuation sled.

5. The loading unit according to claim 1, wherein the pushers include a lateral extension that is elongate in a vertical direction and the cartridge assembly includes T-shaped retention slots, the lateral extension being received in a portion of the T-shaped retention slot.

6. The loading unit according to claim 5, wherein the actuation sled includes a first wedge and a second wedge, and distal translation of the actuation sled causes the first wedge to contact the first camming surface of each pusher in the first row and the second camming surface of each pusher in the second row, and distal translation of the actuation sled causes the second wedge to contact the first camming surface of each pusher in the third row and the second camming surface of each pusher in the fourth row.

7. The loading unit according to claim 1, wherein an outer-most diameter of the end effector is about 5 mm.

8. The loading unit according to claim 1, wherein an outer-most diameter of the end effector is selected from the group consisting of about 4 mm, 5 mm and 8 mm.

9. The loading unit according to claim 1, further comprising a plurality of T-shaped retention slots extending through a tissue-contacting surface of the cartridge assembly.

10. The loading unit according to claim 1, wherein each pusher in the first row is disposed in a first orientation and each pusher in the second row is disposed in a second orientation, the first orientation is offset 180° from the second orientation.

11. The loading unit according to claim 1, wherein each pusher in the first row is the same as each pusher in the second row.

12. The loading unit according to claim 2, wherein the first camming surface is disposed at a first angle, the second camming surface is disposed at a second angle, and the first angle is the same as the second angle.

13. The loading unit according to claim 12, wherein the first angle is between about 20° and about 40°.

14. The loading unit according to claim 2, wherein each pusher includes a body portion including an upper edge configured to engage a fastener, a lateral extension extending perpendicularly from the body portion, a first leg extending in a first direction from the lateral extension and including the first camming surface, and a second leg extending in a second direction from the lateral extension and including the second camming surface.

15. The loading unit according to claim 14, wherein the upper edge of the lateral extension is co-planar with the upper edge of the body portion.

16. A pusher for use with a surgical instrument, comprising:
   a body portion including an upper edge configured to engage a fastener;
   a lateral extension extending perpendicularly from the body portion, an upper edge of the lateral extension is co-planar with the upper edge of the body portion;
   a first leg extending in a first direction from the lateral extension and including a first camming surface; and
   a second leg extending in a second direction from the lateral extension and including a second camming surface.

17. The pusher according to claim 16, wherein the first camming surface is disposed at a first angle, wherein the second camming surface is disposed at a second angle, and wherein the first angle and the second angle are the same.

18. The pusher according to claim 17, wherein the first angle is between about 20° and about 40°.

19. The pusher according to claim 16, wherein the first direction is opposite from the second direction.

20. A loading unit configured for engagement with a surgical instrument, the loading unit comprising:
   a proximal body portion defining a longitudinal axis;
   an end effector disposed in mechanical cooperation with the proximal body portion, the end effector including a cartridge assembly and an anvil assembly, one of the cartridge assembly or the anvil assembly being movable with respect to the other of the cartridge assembly or the anvil assembly between an open position and an approximated position to capture tissue therebetween, the cartridge assembly configured to house fasteners therein, the cartridge assembly including a tissue-contacting surface defining a plurality of T-shaped retention slots;
   an actuation sled longitudinally translatable within the cartridge assembly; and
   pushers disposed within the cartridge assembly, the pushers arranged in first and second rows, each pusher including a camming surface configured for engagement with the actuation sled, wherein the camming surface of each pusher in the first row is longitudinally aligned with the camming surface of each pusher in the second row, the first row of pushers laterally offset from the second row of pushers.

* * * * *